(12) United States Patent
Lake et al.

(10) Patent No.: US 7,700,839 B2
(45) Date of Patent: Apr. 20, 2010

(54) **PASTURE, FORAGE AND SEED PRODUCTION TECHNOLOGY THROUGH POD AND LEAF RETENTION ON ANNUALS OF THE *MEDICAGO* GENUS (ANNUAL MEDICS)**

(75) Inventors: Andrew Wylde Hingston Lake, Daw Park (AU); Rickie Elizabeth Drewry, Hope Valley (AU)

(73) Assignee: Pristine Forage Technologies Pty Ltd., Daw Park, South Australia (AU)

( * ) Notice: Subject to any disclaimer, the term of this patent is extended or adjusted under 35 U.S.C. 154(b) by 382 days.

(21) Appl. No.: 11/049,619

(22) Filed: Feb. 2, 2005

(65) Prior Publication Data
US 2005/0172362 A1 Aug. 4, 2005

(30) Foreign Application Priority Data
Feb. 4, 2004 (AU) .............................. 2004900498

(51) Int. Cl.
*A01H 5/00* (2006.01)
*A01H 1/00* (2006.01)

(52) U.S. Cl. ................. 800/295; 800/260; 800/266; 800/269; 800/270

(58) Field of Classification Search ............... 800/260, 800/266, 269, 270, 295
See application file for complete search history.

(56) References Cited

OTHER PUBLICATIONS

Poelham et al. Breeding Field Crops, 4th ed., 1995.*
Hammond et al. JAOCS 61(11): 1713-1716, 1984.*
Oba et al. Field Crops Research 66: 269-276, 2000.*
Maluszynski et al. Euphytica 85: 303-315, 1995.*
Anon, (1996), "Strand medic, *Medicago littoralis* 'Herald' syn Z-245", Plant Varieties Journal, vol. 9, Issue 2, pp. 49 and 50.
Crawford, E.J. et al (1989). "Breeding annual *Medicago* species for semiarid conditions in southern Australia". Advances In Agronomy, vol. 42, pp. 399 to 437.

* cited by examiner

*Primary Examiner*—Cynthia Collins
*Assistant Examiner*—Keith O. Robinson
(74) *Attorney, Agent, or Firm*—Klauber & Jackson LLC

(57) ABSTRACT

The present invention relates to improved cultivars, varieties, lines or plants of annual medics (*Medicago* genus) wherein the majority of seed pods, upon reaching maturity, remain attached to their respective pedicels. In particular, the present invention relates to improved cultivars, varieties, lines or plants of annual medics (*Medicago* genus), having a mutant form of the gene for pod shedding, thereby resulting in a "pod holding" trait. The invention also extends to methods for isolating such plants. A yet further aspect of the invention relates to a method of transferring the "pod holding" trait from an annual medic having this trait to another annual medic of the genus *Medicago* by a process of controlled cross-breeding. A still further aspect of the invention relates to a method of obtaining plants having the "pod holding" trait from a population of annual medics of the genus *Medicago*.

7 Claims, 2 Drawing Sheets

PASTURE, FORAGE AND SEED PRODUCTION TECHNOLOGY THROUGH POD AND LEAF RETENTION ON ANNUALS OF THE *MEDICAGO* GENUS (ANNUAL MEDICS)

BACKGROUND OF THE INVENTION

The present invention relates to improved cultivars of annual pasture and forage legumes of the *Medicago* genus (annual medics).

The present inventors have had extensive experience and success in the breeding and development of cultivars of pasture legume, in particular cultivars of annuals of the *Medicago* genus. Some years ago, they recognised that a major impediment to adoption and use of *Medicago* cultivars was seed cost, and that a major component of that seed cost related to the difficulty of harvesting and cleaning the seed. This is because, at maturity, the seed pods are dropped from the plant, and harvesting of seed entails vacuum harvesting the pods off the ground. The harvesting process is therefore slow, and requires specialised and powerful equipment, with large fuel inputs.

Accordingly, the present inventors sought to develop a medic that does not drop its seed pods and therefore can be harvested cheaply and efficiently with conventional harvesting equipment. This pod holding characteristic has never been recorded in naturally occurring annual medics.

Pod shedding is a result of growth of a layer of cells across the pedicel (pod stalk) at the base of the pod, which cuts off nutrient flows into the maturing pod and leads to effective separation of the pod from the pedicel. At the slightest disturbance, the pod then drops to the ground under its own weight and, by the time the plant has itself matured, the pod has been shed. Research has indicated that control of development of this abscission layer of cells is genetically controlled.

SUMMARY OF THE INVENTION

The present invention relates to improved cultivars, varieties, lines or plants of annual medics (*Medicago* genus) wherein the majority of seed pods, upon reaching maturity, remain attached to their respective pedicels (this being referred to as the "pod holding" trait). In particular, the present invention relates to improved cultivars, varieties, lines or plants of annual medics (*Medicago* genus), having a mutant form of the gene for pod shedding (ie for formation of an abscission layer between maturing seed pods and their respective pedicels), thereby resulting in the aforementioned "pod holding" trait.

In a further aspect of the invention, seed from known cultivars or wild-type varieties of annual medics (*Medicago* genus) are subjected to treatment with a mutagenic agent, and improved cultivars, varieties, lines or plants having the aforementioned "pod holding" trait are isolated, eg by a selective breeding program. In particular, the mutated seeds are selected for the aforesaid "pod holding" trait (eg by growing the treated seeds, or descendants thereof, to maturity, assessing whether this trait is present, and selecting plants displaying this trait), and plants of the next generation are in turn grown from seeds of those selected plants, and then assessed. This process is repeated to isolate cultivars, varieties, lines or plants wherein the "pod holding" trait is stable and heritable. The mutagenic agent is, in particular, gamma radiation.

In the embodiment described below, selective breeding commenced with the M2 generation. The M2 seed was grown to maturity, and assessed for the "pod holding" trait. Plants of the M3 generation were in turn grown from seeds of selected plants of the M2 generation, and then assessed. This selective breeding process was repeated until the "pod holding" mutation was shown to be stable and heritable.

A yet further aspect of the invention relates to a method of transferring the "pod holding" trait from a cultivar, variety, line or plant having this trait to another annual medic of the genus *Medicago* by a process of controlled cross-breeding of said cultivar, variety, line or plant with said other annual medic and selection of progeny or descendants having the "pod holding" trait. In particular, the method can include the following steps:

(i) cross-breeding said cultivar, variety, line or plant with said other annual medic, and collecting hybrid seed resulting from this cross-breeding;
(ii) planting said hybrid seed and producing F1 hybrid (first generation) plants therefrom;
(iii) allowing the F1 plants to self-pollinate and set seed;
(iv) planting the seed from the F1 plants and producing F2 (second generation) plants therefrom;
(v) assessing the F2 or any later generation of plants for said "pod holding" trait and selecting said F2 or later generation plants having this trait.

A still further aspect of the invention relates to a method of obtaining plants having the "pod holding" trait from a population of annual medics of the genus *Medicago*. That population is derived by controlled or natural cross-breeding of annual medics, where one or more of the population parents carries one or more copies of the gene conferring the "pod holding" trait, and individual plants, progeny or descendants of the said population having the "pod holding" trait are selected. In particular, the method can include the following steps:

(i) obtaining a population derived from controlled or natural cross-breeding of an annual medic where one or more parents of said population have the "pod holding" trait or are progeny or descendants of controlled or natural cross-breeding involving one or more parents having the "pod holding" trait;
(ii) growing plants of the population;
(iii) assessing plants of the population or plants grown from seed harvested from any descendant generation of the population for said "pod holding" trait and selecting plants having this trait.

The progeny or descendants created by either of the aforesaid methods may also be selected for improved mature leaf retention, this being a trait directly associated with the "pod holding" trait.

DETAILED DESCRIPTION OF THE INVENTION

As a base cultivar for mutation treatment, Herald (*M. littoralis*) was used. A description of this base cultivar can be found in Plant Varieties Journal, 1996, Volume 9, Issue 2, page 49.

Chemical mutagenesis, using various doses of sodium azide (as suggested in the scientific literature), was initially trialled. However, after about a year, it was concluded that this treatment was insufficiently effective, as it resulted in high mortality rates, but low rates of mutation, at effective dosages. It was then decided to try irradiation.

Preliminary tests, carried out under the direction of the inventors by the International Atomic Energy Agency Plant Breeding Laboratories, Siebersdorf, Austria, showed that treatment of desiccated seed with between 200 and 300 Gy of gamma radiation (source: Cobalt 60) gave acceptably high levels of mutation, associated with low mortality. The gamma irradiated seed therefore showed higher treatment effects with respect to mutation, at lower rates of mortality, than was the case with chemical mutagenesis; this was confirmed in field trials (as described below).

Accordingly, seed was sent to the aforesaid Laboratories for treatment, and then returned to Australia, where greenhouse testing confirmed levels of treatment-induced mortality, and related growth retardant effects, on surviving M1 (first generation grown after the mutation treatment) plants. These M1 plants numbered about 700 and were derived from about 10 gm of treated seed.

The surviving M1 plants were grown and multiplied to produce about 500 gm of M2 seed. As expected, fertility rates were also significantly reduced as a result of the radiation treatment. Seed harvested from the M1 plants was then sown into the field, to produce 40 to 50,000 plants of generation M2. These were monitored for mutation effects and, in particular, for plants that held onto their pods at maturity.

This resulted in the isolation of approximately 40 plants with various degrees of pod holding. Nearly all (bar three) of these 40 plants exhibited relatively poor pod holding capabilities, but all were progeny tested to test the genetic nature and heritability of the observed pod holding.

All three of the good pod holding M2 plants showed very high heritability of the trait in the M3 and subsequent generations, with clear differences in this trait from all other medic plants, including other selected M2 progenies. There were also lesser differences observed in the strength of pod holding among the three good pod holders and their respective (crossbred and self-pollinated) progenies. One plant and its self-pollinated progeny consistently showed stronger pod holding compared to the other two, and this plant also yielded higher strength pod holders from its cross-bred progeny.

Further testing showed that this pod holding characteristic is recessive and almost certainly due to mutation of a single gene, with the variation in the strength of characteristic expression which was observed in different plants and progenies indicating different mutations of the same gene in the original selections.

Seeds from a cultivar of *Medicago littoralis* having the "pod holding" trait have been deposited on 28 Jan. 2005 at the Australian Medicago Genetic Resources Centre Collection, GPO Box 397, Adelaide SA 5001, Australia, under the deposit number SA 42 891.

The pod holding mutation was found to significantly retard pod shedding in medics, with most pods being held on the vine long after the plant is mature and dried off. Because of the fragile nature of the pedicel and the weight of the pod, some pod shedding can be induced by mechanical disturbance, which is in itself an aid to harvesting, as the pod needs to be separated from the vine.

This trait forms a clear contrast with all other annual medics, where pods are shed even while the plants (and even the pods themselves) are still green, and hence the trait is clearly and easily observed in the field.

As a further and beneficial effect of the mutated gene [hereinafter referred to as the "ph" (for "pod holding") gene], older leaves are also retained on the vine. This is because leaf shedding occurs by the same mechanism, with formation of an abscission layer at the base of each leaflet of the medic trifoliate, leading to leaf drop once the trifoliate is mature. Again, this leaf drop is very pronounced in the normal type of annual medic, with even old or slightly diseased leaves on relatively immature plants being frequently shed. As with pods, leaf drop on mature medics is virtually total once the plant is mature and dried off.

As with pod retention, mature leaf retention on plants with the ph trait is easily seen in the field, and is in marked contrast to leaf shed without the ph trait. The ph trait is readily seen in ph plants, not only in the retention of dead leaves on green plants, but also in their retention on the mature and dried off vine. By way of contrast, plants without the ph trait are left as leafless and pod-less stalks in the dried off state.

The pod holding and leaf holding traits are illustrated in the accompanying photographs (FIGS. 1 to 4), which compare plants which are nearly isogenic (ie nearly genetically identical), except for the mutant ph gene. The photographs were all taken on the same date on plants with identical treatment.

Figure 1:
FIG. 1 shows the normal type of annual medic, with no mature pods or leaves left on the plant.
Figure 2:
FIG. 2 shows the mutant (ph gene) type, with mature, semi-mature and green pods and leaves still on the plant.
Figure 3:
FIG. 3 shows the normal type of annual medic. The ground underneath the plant has both leaves and pods shed from the plant.
Figure 4:
FIG. 4 shows the mutant (ph gene) type. The ground underneath the plant has very little pod or leaf material.

Our field trials have indicated that any substantial mutation of the naturally occurring form of the ph gene, being sufficient to disrupt production of the expression product of that gene, results in at least some degree of the pod holding trait. Cultivars with a sufficient degree of the pod holding trait, and with sufficient heritability of the characteristic, can then be selected, eg by a selective breeding program.

Further, testing has shown that the pod holding trait can be transferred between different annual medics through hybridisation and selection, and that the mutant gene behaves similarly to other nuclear genes within the plant. This enables new pod holding cultivars to be developed through cross breeding and selection.

Hand crosses between normal pod shedding plants and pod holding selections containing the mutant ph gene were made. Hybrid seed was planted and the F1 hybrid (first generation) plants which were produced all shed both mature pod and leaf in the same way as the normal pod shedding plants.

These F1 plants were then allowed to naturally self-pollinate and set seed. This seed was sown to produce an F2 generation. Individual plants were then assessed for pod and leaf holding. Plants with levels of mature pod and leaf holding that were similar to the pod holding parent, and in strong contrast to the pod and leaf shedding parent, all the F1 plants, and their sibling but non-pod holding F2 plants, were readily identifiable in this F2 generation. Approximately one quarter of individuals of the F2 population had this pod holding characteristic. In addition, all individual plants that exhibited either the mature pod holding or the mature leaf holding trait exhibited both traits together in the same plant.

Progeny derived from natural self-pollination of these selected pod and leaf holding plants were pure breeding for that characteristic; ie 100% of plants from subsequent (naturally self-pollinated) generations of the pod and leaf holding selections exhibited the pod and leaf holding trait.

These observations are all consistent with the genetic segregation expected from a cross between two parents that are genetically homozygous and pure breeding for the pod (and leaf) shedding, and the mutant pod (and leaf) holding, characteristics respectively, where the mutant pod (and leaf) holding characteristic is determined by a single recessive gene.

This has been further confirmed by selection within populations created by cross-breeding plants that do not themselves exhibit the "pod holding" trait, but are derived from hybrids or descendants thereof wherein at least one parent of the hybrid exhibits the "pod holding" trait. When these populations are allowed to self-pollinate and the seed is harvested and re-sown, individual progeny plants with the "pod holding" trait are found in subsequent generations. The frequency of occurrence of plants with the "pod holding" trait within these subsequent generations is again consistent with the genetic segregation expected if one of the original parents of the population carried the trait in the heterozygous state as a single recessive (ie unexpressed) gene. Expression of the "pod holding" characteristic in descendant generations of this population arises in those individuals where the recessive gene conferring the "pod holding" trait occurs in the homozygous condition, such occurrence arising through natural genetic segregation within the population.

As the mutant gene will therefore occur more or less randomly within hybrid populations that have at least one parent carrying the mutant ph gene in either the heterozygous or the homozygous state, new pod holding cultivars are developed by selection of different plants with the pod and leaf holding phenotype from within these populations. Plants exhibiting this trait are homozygous for the mutant gene and, being naturally self-pollinating, are thus pure breeding for the pod and leaf holding characteristic.

Using these methods of cross-breeding and selection, we have succeeded in transferring the "pod holding" trait of the present invention from the *Medicago littoralis* cultivar, into which the trait was first introduced, into plants of the species *M. truncatula* and *M. tornata*.

It should be noted that, while the present invention has been exemplified in terms of particular species of annual medic, the methods should be applicable to any annual medic of the genus *Medicago*.

The invention claimed is:

1. A cultivar of *Medicago littoralis* deposited under accession number NCIMB 41621, said cultivar having a mutant form of the gene for pod shedding whereby the majority of seed pods are retained on the plant after the plant is mature and dried off.

2. A method of transferring a "pod holding" trait, whereby the majority of seed pods, upon reaching maturity, remain attached to their respective pedicels, from the cultivar according to claim 1, said method entailing controlled cross-breeding of said cultivar with another annual medic and selection of progeny or descendants having said "pod holding" trait.

3. The method according to claim 2, wherein progeny or descendants are also selected for improved mature leaf retention.

4. The method according to claim 2, including the following steps:
 (i) cross-breeding said cultivar of the genus *Medicago* with said other annual medic, and collecting hybrid seed resulting from this cross-breeding;
 (ii) planting said hybrid seed and producing F1 hybrid (first generation) plants therefrom;
 (iii) allowing the F1 plants to self-pollinate and set seed;
 (iv) planting the seed from the F1 plants and producing F2 (second generation) plants therefrom; and
 (v) assessing the F2 or any later generation of plants for said "pod holding" trait and selecting said F2 or later generation plants having this trait.

5. The method according to claim 4, wherein progeny or descendants are also selected for improved mature leaf retention.

6. A method of obtaining a cultivar having the "pod holding" trait of the cultivar of *Medicago littoralis* deposited under accession number NCIMB 41621, whereby the majority of seed pods, upon reaching maturity, remain attached to their respective pedicels, from a population of annual medics of the genus *Medicago*, where one or more of the population parents is the cultivar of *Medicago littoralis* deposited under accession number NCIMB 41621, said method including the steps of deriving said population by controlled or natural cross-breeding of an annual medic of the genus *Medicago*, and selecting individual plants, progeny or descendants of said population having said "pod holding" trait.

7. The method according to claim 6, wherein progeny or descendants are also selected for improved mature leaf retention.

* * * * *